United States Patent
Mihalik

(12) 
(10) Patent No.: US 6,492,340 B2
(45) Date of Patent: Dec. 10, 2002

(54) PARASITICIDAL FORMULATION AND A METHOD OF MAKING THIS FORMULATION

(75) Inventor: Richard Mihalik, St. Joseph, MO (US)

(73) Assignee: Phoenix Scientific, Inc., St. Joseph, MO (US)

(*) Notice: Subject to any disclaimer, the term of this patent is extended or adjusted under 35 U.S.C. 154(b) by 0 days.

(21) Appl. No.: 09/964,154

(22) Filed: Sep. 26, 2001

(65) Prior Publication Data

US 2002/0010142 A1 Jan. 24, 2002

Related U.S. Application Data

(62) Division of application No. 09/504,830, filed on Feb. 16, 2000, now Pat. No. 6,340,672.

(51) Int. Cl.[7] .................. A01N 43/04; A01N 43/16; A01N 31/00
(52) U.S. Cl. .................. 514/30; 514/458; 514/730
(58) Field of Search ................ 514/30, 458, 730

(56) References Cited

U.S. PATENT DOCUMENTS 4,395,407 A    7/1983  Ballany et al.
6,054,140 A    4/2000  Lamberti
6,193,989 B1 * 2/2001  Lamberti .................. 424/405

FOREIGN PATENT DOCUMENTS

WO    8400095    1/1984

* cited by examiner

Primary Examiner—Kevin E. Weddington
(74) Attorney, Agent, or Firm—Stinson Morrison Hecker LLP

(57) ABSTRACT

A parasiticidal formulation is provided. This formulation includes a pyrrolidone solvent, a bridging solvent, and an parasiticidal agent. One or more parasiticidal agents may be included in the formulation. Preferably, the formulation contains both closantel and ivermectin. Another aspect of the present invention is a method of making this parasiticidal formulation. This method includes mixing a pyrrolidone solvent and a bridging solvent to form a solvent solution and adding one or more parasiticidal agents to the solvent solution. A further aspect of the present invention is a method for administering the parasiticidal formulation of the present invention to an animal. This method of administration includes providing the parasiticidal formulation described above and applying this formulation to the skin of an animal, wherein the formulation is absorbed through the animal's skin.

4 Claims, No Drawings

PARASITICIDAL FORMULATION AND A METHOD OF MAKING THIS FORMULATION

CROSS-REFERENCE TO RELATED APPLICATIONS

This is a division of Application Ser. No. 09/504,830, filed Feb. 16, 2000, now U.S. Pat. No. 6,340,672.

BACKGROUND OF THE INVENTION

The present invention relates to a parasiticidal formulation and a method for making the formulation. More specifically, the present invention relates to a parasiticidal formulation for use in veterinary applications.

Currently, closantel, a parasiticidal agent, is available in an injectable form or as an oral drench. One disadvantage with these closantel parasiticidal formulations is that they are not available in a pour-on form.

Ivermectin, another parasiticidal agent which kills different parasites from closantel, may be purchased in an injectable form, as a pour-on formulation, in a paste form, as an oral drench, or in a chewable form. The ivermectin injectable formulations currently available contain glycerol formal or propylene glycol to dissolve the ivermectin. The ivermectin pour-on formulations currently available contain isopropyl alcohol or a mixture of caprylic acids and caprylic esters to dissolve the ivermectin.

One disadvantage with both injectable and pour-on ivermectin formulations currently available is that none of these formulations will dissolve closantel and like parasiticidal formulations in concentrations sufficient to be useful. Another disadvantage with the ivermectin pour-on formulations available is that they only have up to a 0.5% weight per volume (w/v) concentration of ivermectin.

Additionally, a disadvantage with parasiticidal formulations currently available is that closantel and ivermectin are not available in a single formulation, and therefore a broadened spectrum of parasite protection is not available in a single formulation. Still further, parasiticidal agents, including, but not limited to closantel and ivermectin, cannot be combined in pour-on formulations currently available in a manner that keeps both parasiticidal agents in solution.

In order to overcome these disadvantages, a parasiticidal formulation containing an effective solvent delivery system that allows one or more parasiticidal agents to dissolve, especially closantel and ivermectin in combination, is needed. In addition, the resulting parasiticidal formulation should be usable in a pour-on or an injectable form. Still further, the solvent delivery system should be able to hold larger amounts of parasiticidal agents than prior formulations.

SUMMARY OF THE INVENTION

It is an object of the present invention to provide a parasiticidal formulation containing more than one parasiticidal agent or a larger amount of a single parasiticidal agent than conventional formulations that may be a administered as a pour-on product in order to facilitate easier administration of the parasiticidal formulation.

It is another object of the present invention to provide a parasiticidal formulation that contains at least two different parasiticidal agents so as to obtain a broadened spectrum of parasite protection.

It is a further object of the present invention to provide a method of making a parasiticidal formulation that achieves the foregoing objects.

Still another object of the present invention is to provide a method for administering a parasiticidal formulation that achieves the foregoing objects.

According to the present invention, the foregoing and other objects are achieved by a pour-on or an injectable parasiticidal formulation that includes a mixture of a pyrrolidone solvent, a bridging solvent and at least one parasiticidal agent. One or more parasiticidal agents may be included in the formulation. Preferably, the formulation contains both closantel and ivermectin. Another aspect of the present invention is a method of making this parasiticidal formulation. This method includes mixing a pyrrolidone solvent and a bridging solvent to form a solvent solution and adding one or more parasiticidal agents to the solvent solution. A further aspect of the present invention is a method for administering the parasiticidal formulation of the present invention to an animal. This method of administration includes providing the parasiticidal formulation described above and applying this formulation to the skin of an animal, wherein the formulation may be absorbed through the animal's skin.

Additional objects, advantages and novel features of the invention will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF THE PREFERRED EMBODIMENT

The parasiticidal formulation of the present invention is an effective pour-on or injectable formulation for protection against parasites. The formulation includes a solvent delivery system and one or more parasiticidal agents. The solvent delivery system includes a mixture of a pyrrolidone solvent and a bridging solvent. This mixture provides a unique solvent system which allows one or more parasiticidal agents to dissolve effectively when added to the solvents.

The pyrrolidone solvent that may be used in the formulation of the present invention includes, but is not limited to, N-methyl-2-pyrrolidone, 2-pyrrolidone, N,5-dimethyl-2-pyrrolidone, 3,3-dimethyl-2-pyrrolidone, N-ethyl-2-pyrrolidone, N-ethoxy-2-pyrrolidone, N-ethylene-2-pyrrolidone, 1-pyrrolidone, or any combinations thereof. Preferably, the pyrrolidone solvent is N-methyl-2-pyrrolidone or 2-pyrrolidone. The pyrrolidone solvent desirably is present in the solvent delivery system in an amount effective, in combination with a bridging solvent, for dissolving a therapeutic amount of one or more parasiticidal agents.

The bridging solvent that may be used in the formulation of the present invention includes, but is not limited to, diethylene glycol monobutyl ether (DGME), benzyl benzoate, isopropyl alcohol, xylenes, or any combinations thereof. If xylenes are used, usually a combination of ortho-xylene, meta-xylene and para-xylene is used. The bridging solvent aids in dissolving the parasiticidal agents and acts to carry the formulation through an animal's skin once it is applied to the skin. If 2-pyrrolidone is used as the pyrrolidone solvent, then preferably xylenes are used as the bridging solvent. If a pyrrolidone solvent other than 2-pyrrolidone is used, then the preferred bridging solvent is DGME. In any event, the solvent delivery system must include an amount of the bridging solvent that is effective, in combination with the pyrrolidone solvent, to dissolve a therapeutic amount of the active parasiticidal agent or agents.

The combination of a pyrrolidone solvent and a bridging solvent to form the unique solvent delivery system of the present invention allows one or more parasiticidal agents to dissolve. The solvent system dissolves the parasiticidal agents and keeps them in solution. The solvent delivery system also functions to transport one or more parasiticidal agents into an animal so that the agent or agents may interact therapeutically with parasites in the animal.

The parasiticidal agents that may be used in the formulation of the present invention include, but are not limited to, closantel, oxyclozanide, praziquantel, pyrantels, tetrahydropyrimidines, probenzimidazoles, imidazothiazoles, macrocyclic lactones, benzimadizoles, tetramisoles, avermectins, epsiprantel, morantel, febantel, netobimin, clorsulon, bunamidine, nitroscanate, melarsomine, amidines, benzoyl urea derivatives, carbamates, nitroquanidines, pyrazoles, pyrethrins, pyrethroids, pyriproxyfen, acylhydrazones and any combinations thereof.

An example of a pyrantel that may be used is pyrantel pamoate. Examples of benzimadizoles that may be used include, but are not limited to, mebendazole, oxibendazole, fenbendazole, oxfendazole, triclabendazole, flubendazole, ricobendazole, thiabendazole, and albendazole. Preferably, if a tetramisole is used, it is levamisole. Examples of avermectins that may be used include, but are not limited to, ivermectin, moxidectin, doramectin, eprinomectin, and milbemycin. Preferably, a combination of ivermectin and closantel is used as the parasiticidal agent in the formulation. Ivermectin kills a variety of internal and external parasites; a number of worms including stomach worms, intestinal worms, lungworms, barber's pole worms, lice, and mites. Closantel kills adult and immature barber's pole worms, liver flukes, and all stages of nasal bot in sheep. Most preferably, the formulation contains ivermectin and closantel in about a 1:10 ratio.

As discussed above, closantel and ivermectin each provide protection against different species of parasites. Thus, when closantel and ivermectin are combined in a single parasiticidal formulation, the formulation provides protection against a broader spectrum of parasites than a formulation containing either parasiticidal agent alone. Additionally, because the solvent delivery system of the present invention effectively dissolves both closantel and ivermectin, if either active ingredient is used in the absence of the other, the solvent delivery system of the present invention may still be used. When used with a single parasiticidal agent, including, but not limited to ivermectin or closantel, the solvent delivery system of the present invention may allow the parasiticidal agent to dissolve at a higher concentration than formulations currently available. For example, an ivermectin formulation with a concentration of ivermectin from about 1–5% w/v or higher may be made. Thus, the solvent delivery system of the present invention allows for several formulations, each manufactured to provide protection against a targeted parasite population.

The preferred total amount of parasiticidal agent in the formulation of the present invention may be about 0.1–15% w/v, whether used singularly or in combination. Preferably, the formulation of the present invention includes about 1–8% w/v parasiticidal agent.

When using closantel and ivermectin in combination, the parasiticidal formulation of the present invention preferably may include about 1–10% w/v closantel and about 0.1–5% w/v ivermectin. More preferably, the formulation of the present invention may include about 3–7% w/v closantel and about 0.3–0.7% w/v ivermectin. Most preferably, the formulation of the present invention may include about 5% w/v closantel and about 0.5% w/v ivermectin.

If the chosen pyrrolidone solvent is N-methyl-2-pyrrolidone, the parasiticidal formulation of the present invention preferably may include about 5–90% w/v N-methyl-2-pyrrolidone. More preferably, it includes about 30–50% w/v N-methyl-2-pyrrolidone. Most preferably, it may include about 40–45% w/v N-methyl-2-pyrrolidone. However, when increased amounts of closantel are used in the formulation, the amount of N-methyl-2-pyrrolidone may also be increased to ensure that the closantel dissolves. Thus, amounts at the higher ends of the ranges given are used.

If the chosen pyrrolidone solvent is 2-pyrrolidone, the parasiticidal formulation of the present invention preferably may include about 15–90% w/v 2-pyrrolidone. More preferably, it may include about 50–80% w/v 2-pyrrolidone. Most preferably, it may include about 70% w/v 2-pyrrolidone.

If any pyrrolidone solvent other than N-methyl-2-pyrrolidone or 2-pyrrolidone is chosen, the parasiticidal formulation of the present invention preferably may include about 10–90% w/v pyrrolidone solvent. More preferably, it may include about 30–70% w/v pyrrolidone solvent.

If the chosen bridging solvent is DGME, the parasiticidal formulation of the present invention may preferably include about 10–90% w/v DGME. More preferably, it may include about 25–75% w/v DGME. Most preferably, it may include about 50% w/v DGME. If any bridging solvent other than DGME is chosen, either singularly or in combination, the parasiticidal formulation of the present invention preferably may include about 10–90% w/v bridging solvent. More preferably, it may include about 30–70% w/v bridging solvent. Most preferably, it may include about 50% w/v bridging solvent.

While the solvent delivery system and a parasiticidal agent are the only components necessary in the formulation of the present invention, a number of optional ingredients may be added to enhance certain properties of the formulation. One such optional ingredient is a stabilizer which acts to enhance the stability of the parasiticidal formulation. Stabilizers that may be used in the formulation of the present invention include, but are not limited to, vitamin $B_{12}$, vitamin E acetate, niacinamide, ascorbic acid, butylated hydroxyaniline, thioctic acid, sorbic acid, sodium formaldehyde sulfoxylate, butylated hydroxytoluene, or any combinations thereof. Preferably, vitamin $B_{12}$ and vitamin E acetate, either singularly or in combination, are used as stabilizers in the formulation of the present invention because they are the most effective in preserving the active ingredients.

If vitamin $B_{12}$ is chosen as a stabilizer for the formulation, the parasiticidal formulation of the present invention preferably may include about 0.005–1% w/v vitamin $B_2$. More preferably, it may include about 0.01–0.5% w/v vitamin $B_{12}$. Most preferably, it may include about 0.1% w/v vitamin $B_{12}$.

If vitamin E acetate is chosen as a stabilizer for the formulation, the parasiticidal formulation of the present invention preferably may include about 0.05–5% w/v vitamin E acetate. 16–4 More preferably, it may include about 0.5–1.5% w/v vitamin E acetate. Most preferably, it may include about 1% w/v vitamin E acetate.

If any stabilizer other than vitamin $B_{12}$ or vitamin E acetate is used in the formulation, the formulation of the present invention preferably may include about 0.005%–15% w/v stabilizer.

More preferably, it may include about 0.05–3% w/v stabilizer. These ranges of stabilizers also may apply if two or more of the stabilizers are used in combination, such as when vitamin $B_{12}$ and vitamin E acetate are used in combination.

Another optional ingredient that may be included in the formulation of the present invention is a solubility agent. Solubility agents of the present invention may include, but are not limited to, mixtures of caprylic acids and esters, ethyl oleate, propylene glycol, Arachis oil (peanut oil), or any combinations thereof. The mixtures of caprylic acids and esters may contain from about 99% acids to about 99% esters. Solubility agents aid in dissolving the active ingredients of the formulation, but also aid in spreading the formulation across an animal's skin once it has been poured over the skin, making the formulation less aggressive to the skin. Still further, because each of these solubility agents are oily substances used in the formulation, they help the skin retain moisture.

The parasiticidal formulation of the present invention preferably may include about 5–50% w/v solubility agent. More preferably, the formulation of the present invention may include about 10–35% w/v solubility agent. Most preferably, the formulation of the present invention may include about 20% w/v solubility agent.

Another ingredient that optionally may be added to the formulation of the present invention is a colorant. Colorants give the formulation a more consistent color and aid an observer in determining what areas of an animal's skin have been treated. A colorant may be added to the parasiticidal formulation of the present invention in an amount sufficient that the formulation poured onto the animal's skin can be seen. In addition, water may be added to the formulation of the present invention. In fact, it may be necessary to add water to the formulation if a colorant is added so that the colorant is adequately dispersed. Further, a pH stabilizer may be added to the parasiticidal formulation of the present invention to prevent hydrolysis. Examples of pH stabilizers that may be used in conjunction with the present invention include, but are not limited to, triethanolamine and diethanolamine.

One preferred formulation of the present invention includes N-methyl-2-pyrrolidone, DGME, closantel, and ivermectin. Another preferred formulation of the present invention includes 2-pyrrolidone, xylenes, closantel, and ivermectin. A highly preferred formulation of the present invention is described in Example 1.

The parasiticidal formulation of the present invention is made by combining a pyrrolidone solvent, a bridging solvent, and one or more parasiticidal agents to form a mixture.

Preferably, closantel and ivermectin may be used in combination as the parasiticidal agents. The order in which components are added in making the formulation is not critical. The formulation may optionally be heated to between about 40° and 80° C. continuously or intermittently during its preparation in order to dissolve the components more quickly. If vitamin $B_{12}$ is used as a stabilizer, it is recommended that the formulation may be heated to about 500° C. prior to adding the vitamin $B_{12}$.

Preferably, a portion of the pyrrolidone solvent, the bridging solvent, or the solubility agent may be added last so that a specific quantity of parasiticidal formulation may be obtained and to ensure that all ingredients dissolve. This process can be scaled to make any desired quantity of the formulation.

One preferred method of making the parasiticidal formulation of the present invention includes placing a quantity of pyrrolidone solvent in a vessel and warming it to about 50° C. Next, a stabilizer is added, and the resulting solution is cooled to room temperature. The bridging solvent is then added and mixed into the solution for an effective period of time. Optionally, a second stabilizer may then be added and mixed until all ingredients are adequately dissolved. Following this, ivermectin is added and mixed into the solution until it is dissolved. Closantel is then added, and the mixture is agitated until a portion of the closantel is dissolved. The closantel likely will not completely dissolve. Thus, it will be necessary to add an additional portion of pyrrolidone solvent to ensure that all components adequately dissolve.

The parasiticidal formulation of the present invention may be administered as a pour-on product or as an injectable formulation to any animal. Preferably, it is administered as a pour-on product. It is especially useful for cattle, horses, sheep, goats, and pigs. Most preferably, it is administered to cattle. It may be poured over an animal's back or may be poured on any other body part of an animal that needs treatment. Preferably, it may be administered in a dosage of about 0.020.4 milliliters of formulation per kilogram of animal. More preferably, it may be administered in a dosage of about 0.02–0.3 milliliters of formulation per kilogram of animal. Most preferably, it may be administered in a dosage of about 0.02–0.25 milliliters of formulation per kilogram of animal.

The following are examples of various parasiticidal formulations and methods of making these formulations that are within the scope of this invention. These examples are not meant in any way to limit the scope of this invention.

EXAMPLE 1

N-methyl-2-pyrrolidone was added to a vessel and warmed to 500° C. Agitation began. With continued agitation, a quantity of vitamin $B_{12}$ amounting to 0.1% w/v of the final formulation was added to the solvent and mixed with it until the vitamin $B_{12}$ dissolved. The resulting solution was then cooled to room temperature. A quantity of DGME amounting to 50% w/v of the final formulation was then added and mixed into the solution. Next, vitamin E acetate was added in a quantity amounting to 1% w/v of the final formulation, and the resulting solution was mixed until all ingredients were adequately dissolved. With continued agitation, a quantity of ivermectin amounting to 0.5% w/v of the final formulation was added and mixed into the solution until dissolved. Closantel was then added in a quantity amounting to 5% w/v of the final formulation, and the mixture was agitated to dissolve a portion of the closantel. With continued agitation, a supplemental amount of N-methyl-2-pyrrolidone was added in an amount sufficient to completely dissolve the closantel. The total amount of N-methyl-2-pyrrolidone used made up the balance of the formulation.

EXAMPLE 2

A quantity of xylenes was added to a vessel. To the xylenes, a quantity of 2-pyrrolidone amounting to 70% w/v of the final formulation was added and agitation began. With continued agitation, a quantity of ivermectin amounting to 0.5% w/v of the final formulation was added and mixed into the solution until dissolved. Next, closantel was added in a quantity amounting to 5% w/v of the final formulation, and the mixture was agitated to dissolve a portion of the closantel. With continued agitation, a supplemental amount of xylenes was added in an amount sufficient to completely dissolve the closantel. The total amount of xylenes used made up the balance of the formulation.

EXAMPLE 3

A quantity of xylenes was added to a vessel. Agitation began. With continued agitation, a quantity of N-methyl-2-pyrrolidone amounting to 18.2% w/v of the final formulation was added. Next, a quantity of a mixture of caprylic acids and esters (obtained from Croda, Inc. of Parsippany, New Jersey under the tradename Crodamol Cap™) amounting to 18.2% w/v of the final formulation was added and mixed with the solution until the Crodamol Cap™ dissolved. Subsequently, a quantity of vitamin E acetate amounting to 0.93% w/v of the final formulation was added. With continued agitation, diethanolamine was added in a quantity amounting to 0.16% w/v to the solution and mixed until dissolved. Next, a quantity of Arachis oil amounting to 16% w/v of the final formulation was added and mixed until dissolved. Following this, a quantity of ivermectin amounting to 0.45% w/v of the final formulation was added and mixed into the solution until dissolved. Closantel was then added in a quantity amounting to 4.5% w/v, and the mixture was agitated for a time sufficient to dissolve a portion of the closantel. With continued agitation, a supplemental amount of xylenes was added in an amount sufficient to completely dissolve the closantel. The total amount of xylenes used made up the balance of the formulation.

EXAMPLE 4

A quantity of N-methyl-2-pyrrolidone was added to a vessel. Agitation began. With continued agitation, a quantity of isopropyl alcohol amounting to 20% w/v of the final formulation was added, and the two solvents were mixed into solution. Next, a quantity of ethyl oleate amounting to 20% w/v of the final formulation was added, and the mixture was agitated until all ingredients were adequately dissolved. Subsequently, a quantity of DGME amounting to 20% w/v of the final formulation was added. Next, a quantity of benzyl benzoate amounting to 20% w/v of the final formulation was added. Following this, a quantity of vitamin E acetate amounting to 1% Age w/v of the final formulation was added, and the solution mixed until all components adequately dissolved. With continued agitation, a quantity of ivermectin amounting to 0.5% w/v of the final A formulation was added. Subsequently, a quantity of closantel amounting to 5% w/v of the final formulation was added, and the mixture was agitated to dissolve a portion of the closantel. With continued agitation, a supplemental amount of N-methyl-2-pyrrolidone was added in an amount sufficient to completely dissolve all of the closantel. The total amount of N-methyl-2-pyrrolidone used made up the balance of the formulation.

EXAMPLE 5

A quantity of N-methyl-2-pyrrolidone was added to a vessel. Agitation began. To the N-methyl-2-pyrrolidone, a quantity of benzyl benzoate amounting to 44.3% w/v of the final formulation was added, and the mixture was agitated to ensure all ingredients dissolved. With continued agitation, a quantity of ethyl oleate amounting to 30% w/v of the final formulation was added. Next, a quantity of ivermectin amounting to 0.5% w/v of the final formulation was added, and the mixture was agitated until all of the ivermectin had dissolved. Next, a quantity of closantel amounting to 5% w/v of the final formulation was added, and the mixture was agitated to dissolve a portion of the closantel. With continued agitation, a supplemental amount of N-methyl-2-pyrrolidone was added in a quantity sufficient to dissolve all of the closantel. The total amount of N-methyl-2-pyrrolidone made up the balance of the formulation.

EXAMPLE 6

A quantity of N-methyl-2-pyrrolidone was added to a vessel. Agitation began. With continued agitation, a quantity of a mixture of caprylic acids and esters (obtained from Croda, Inc. of Parsippany, New Jersey under the tradename Crodamol Cap™) amounting to 18% w/v of the final formulation was added, and the mixture was agitated to ensure that all ingredient dissolved. Next, a quantity of isopropyl alcohol amounting to 30% w/v of the final formulation was added and the mixture was agitated until all ingredients were adequately dissolved. Following this, a quantity of diethanolamine amounting to 0.05% w/v of the final formulation was added. Next, a quantity of ivermectin amounting to 0.5% w/v of the final formulation was added and the mixture was agitated until all components were adequately dissolved into solution. With continued agitation, a quantity of closantel amounting to 5% w/v of the final formulation was added, and the mixture was agitated to dissolve a portion of the closantel. With continued agitation, a supplemental amount of N-methyl-2-pyrrolidone was added in an amount sufficient to completely dissolve all of the closantel. The total amount of N-methyl-2-pyrrolidone made up the balance of the formulation.

EXAMPLE 7

A quantity of propylene glycol was added to a vessel. Agitation began. With continued agitation, a quantity of N-methyl-2-pyrrolidone amounting to 20% w/v of the final formulation was added. Next, a quantity of ethyl oleate amounting to 20% w/v of the final formulation was added, and the mixture was agitated until all ingredients were adequately dissolved. Following this, a quantity of vitamin E acetate amounting to 1% w/v of the final formulation was added. With continued agitation, a quantity of diethanolamine amounting to 0.17% w/v of the final formulation was added. Next, a quantity of xylenes amounting to 40% w/v of the final formulation was added. Next, a quantity of ivermectin amounting to 0.5% w/v of the final formulation was added. Next, a quantity of closantel amounting to 5% w/v of the final formulation was added, and the mixture was agitated to dissolve a portion of the closantel. With continued agitation, a supplemental amount of propylene glycol was then added in an amount sufficient to completely dissolve all of the closantel. The total amount of propylene glycol made up the balance of the formulation.

EXAMPLE 8

A quantity of N-methyl-2-pyrrolidone was added to a vessel. Agitation began. With continued agitation, a quantity of DGME amounting to 40% w/v of the final formulation was added.

Next, a quantity of propylene glycol amounting to 10% w/v of the final formulation was added, and the mixture was agitated until all components were adequately dissolved. Subsequently, a quantity of vitamin E acetate amounting to 1% w/v of the final formulation was added. With continued agitation, a quantity of a mixture of caprylic acids and esters (obtained from Croda, Inc. of Parsippany, N.J. under the tradename Crodamol Cap™) amounting to 20% w/v of the final formulation was added. Next, a quantity of diethanolamine amounting to 0.05% w/v of the final formulation was added. Following this, a quantity of FD&C Blue #1 amounting to 0.02% w/v of the final formulation was added. A quantity of sterile water amounting to 0.2% w/v of the final formulation was then added. With continued agitation, a quantity of ivermectin amounting to 0.5% w/v of the final formulation was added. Next, a quantity of closantel amounting to 5% w/v of the final formulation was added, and the mixture was agitated to dissolve a portion of the closantel.

With continued agitation, a supplemental amount of N-methyl-2-pyrrolidone was then added in an amount sufficient to completely dissolve all of the closantel. The total amount of N-methyl-2-pyrrolidone made up the balance of the formulation.

From the foregoing, it will be seen that this invention is one that is well adapted to attain all the ends and objects herein above set forth together with other advantages which are obvious and inherent to the formulation. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

I claim:

1. A method for treating an animal having parasites, comprising:

administering to said animal a parasiticidal formulation comprising a mixture of at least one parasiticidal agent, at least one pyrrolidone solvent that comprises about 10–90% w/v of said formulation, and at least one bridging solvent selected from the group consisting of diethylene glycol monobutyl ether, benzyl benzoate, isopropyl alcohol, xylenes, and combinations thereof.

2. The method of claim 1, wherein said parasiticidal formulation is poured onto the skin of said animal and is absorbed through said skin.

3. The method of claim 2, wherein said formulation is poured onto the skin of said animal in an amount of about 0.02–0.3 milligrams per kilogram of animal.

4. The method of claim 1, wherein said parasiticidal formulation is injected through the skin of said animal.

* * * * *

UNITED STATES PATENT AND TRADEMARK OFFICE
CERTIFICATE OF CORRECTION

PATENT NO. : 6,492,340 B2  Page 1 of 1
DATED : December 10, 2002
INVENTOR(S) : Richard Mihalik It is certified that error appears in the above-identified patent and that said Letters Patent is hereby corrected as shown below:

<u>Column 4,</u>
Line 57, delete "$B_2$" and insert -- $B_{12}$ -- therefor.
Line 63, delete "16-4".

<u>Column 5,</u>
Line 61, delete "500º" and insert -- 50º -- therefor.

<u>Column 6,</u>
Line 23, insert -- – -- between "0.02" and "0.4".
Line 37, delete "500º" and insert -- 50º -- therefor.

<u>Column 7,</u>
Line 43, delete "Age".
Line 46, delete "A" between "final" and "formulation".

Signed and Sealed this

Eleventh Day of November, 2003

JAMES E. ROGAN
*Director of the United States Patent and Trademark Office*